United States Patent
Gammons

(10) Patent No.: US 7,357,788 B2
(45) Date of Patent: Apr. 15, 2008

(54) REINFORCED MEDICAL PROBE COVER

(75) Inventor: Clifford Eugene Gammons, Loudon, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 268 days.

(21) Appl. No.: 10/775,775

(22) Filed: Feb. 9, 2004

(65) Prior Publication Data

US 2005/0187520 A1    Aug. 25, 2005

(51) Int. Cl.
*A61M 5/00* (2006.01)
(52) U.S. Cl. .................. 604/171; 600/121
(58) Field of Classification Search .......... 604/171, 604/124; 600/124, 121; 374/158
See application file for complete search history.

(56) References Cited

U.S. PATENT DOCUMENTS

| | | | |
|---|---|---|---|
| 3,308,940 A | 3/1967 | Morris | |
| 3,809,230 A | 5/1974 | Poncy | |
| 3,812,769 A * | 5/1974 | Barnes et al. | 493/196 |
| 3,847,280 A | 11/1974 | Poncy | |
| 4,062,239 A | 12/1977 | Fowler et al. | |
| 4,140,127 A * | 2/1979 | Cianci et al. | 604/171 |
| 4,164,285 A | 8/1979 | Dorman | |
| 4,165,000 A * | 8/1979 | Poncy | 206/306 |
| 4,197,944 A | 4/1980 | Catlin | |
| 4,241,828 A | 12/1980 | Bourdelle et al. | |
| 4,246,909 A * | 1/1981 | Wu et al. | 600/575 |
| 4,614,442 A | 9/1986 | Poncy | |
| 4,684,018 A | 8/1987 | Jarund | |
| 4,757,381 A | 7/1988 | Cooper et al. | |
| 4,823,949 A | 4/1989 | Bala | |
| 5,069,337 A | 12/1991 | Bala | |
| 5,667,068 A * | 9/1997 | Weaver | 206/363 |
| 5,769,224 A | 6/1998 | Poncy et al. | |
| 5,795,632 A | 8/1998 | Buchalter | |
| 6,224,543 B1 * | 5/2001 | Gammons et al. | 600/124 |

* cited by examiner

*Primary Examiner*—Nicholas D. Lucchesi
*Assistant Examiner*—Laura Bouchelle
(74) *Attorney, Agent, or Firm*—Knox Patents; Thomas A. Kulaga

(57) ABSTRACT

A cover adapted to be received on the distal end of a medical probe or instrument such as an endoscope in such a manner as to not require the application of a retainer. The cover is constructed of two panel members secured one to the other along their respective sides. A throat is defined proximate the first end and is adapted to closely receive the distal end of the medical probe. The first ends of each of the panels are folded over to define a double thickness of material. The first panel member first end extends beyond the second panel member first end to define an extended portion, which provides a mechanism whereby the distal end of the medical probe is easily inserted into the first end of the cover. The second end of the cover is inverted to assist in the application of the cover of the medical probe.

16 Claims, 3 Drawing Sheets

REINFORCED MEDICAL PROBE COVER

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

The present invention pertains to the field of medical probes. More particularly, the present invention is directed to a probe cover having reinforced layers for covering a medical probe prior to insertion into a sterile field.

2. Description of the Related Art

In the medical field, it is well know to use invasive probes for many various applications. Typical medical probes include, but are mot limited to, endoscopes, ultra-sound probes, rectal or vaginal probes, esophageal probes, as well as surgical instruments. Such medical probes are manipulated from either a sterile or non-sterile field, with the insertion end of the probe disposed within a sterile field. In so placing the probe, it is necessary that the portion of the probe in the sterile field be maintained as sterile. Accordingly, it is known in the art to provide a sheath or cover over the insertion end of probe prior to insertion into the sterile field. Application of the cover onto the probe is normally followed with application of an elastic gasket or a restraining band around one end of the cover to retain the cover thereon.

FIGS. 1 and 2 illustrate one device of the prior art. A sheath 10 for receipt on the end of an endoscope 40 or other medical probe is fabricated from a single layer of flexible material. Typically, the material is a medical grade plastic. The sheath 10 defines a tubular configuration defining a receiving end 12 configured to receive a distal end 42 of the endoscope 40. To this extent, an opening 14 is defined by the receiving end 12 for receiving the endoscope distal end 42. A throat 16 is defined a selected distance from the receiving end 12. The throat 16 is adapted to closely receive the endoscope distal end 42. A sleeve portion 18 is defined between the throat 16 and the distal end 20 of the sheath 10.

A typical sheath 10 is fabricated from a single thickness of flexible plastic film, which, in one tested device, provides approximately 0.35 pounds of tensile strength. While this strength is capable of preventing puncture or other destruction of the sheath 10, it is insufficient to retain the sheath 10 on the endoscope 40 without assistance. Accordingly, a retainer 28 is provided to maintain the position of the sheath 10 on the endoscope 40 once positioned. The retainer 28 is typically an elastomeric or rubber band.

As best illustrated in FIG. 2, the endoscope first end 42 is inserted into the receiving end 12 and through the throat 16. The retainer 28 is then placed over the throat 16 of the sheath 10. The sleeve portion 18 is then inverted over the endoscope 40 to reveal the distal end 42 and the inner surface of the sleeve portion 18, both of which are maintained as sterile.

While the retainer 28 serves to maintain the position of the sheath 10 on the endoscope 40, it creates a raised portion having a height depicted at 26. This raised portion 26 must be taken into account when determining where the endoscope 40 or other medical instrument is to be inserted into the patient. The raised portion 26 can require a larger surgical opening in certain situations, or can create additional discomfort to a patient during insertion and removal into a patient's natural body opening. The retainer 28 also has a tendency to move along the length of the endoscope 40 due to the interference between the raised portion 26 and the patient. It is also known that the application of such a retainer 28 can be difficult due to the required tensile strength and the small size thereof. The retainer 28 is, in certain situations, difficult to place while maintaining a sterile field including the distal end 42 of the endoscope 40 and the interior surface of the sleeve portion 18 of the sheath 10.

Prior art devices have normally involved the mounting of a fully extended sheath onto a carrier. In order to extend the probe into the entire length of the sheath, the medical technician or doctor will insert the probe through the sheath opening and slowly manipulate the tip of the probe such that it travels through the sheath length to its nose. This process can result in inadvertent contact with the wall of the sheath which will engage or become in direct contact with the patient.

Other devices have been developed to overcome these and similar problems associated with the manufacture and application of medical probe sheaths. Typical of the art are those devices disclosed in the following U.S. Patents:

| Pat. No. | Inventor(s) | Issue Date |
| --- | --- | --- |
| 3,308,940 | T. Morris, Jr. | Mar. 14, 1967 |
| 3,809,230 | G. W. Poncy | May 7, 1974 |
| 3,847,280 | G. W. Poncy | Nov. 12, 1974 |
| 4,062,239 | C. F. Fowler, et al. | Dec. 13, 1977 |
| 4,164,285 | H. P. Dorman | Aug. 14, 1979 |
| 4,165,000 | G. W. Poncy | Aug. 21, 1979 |
| 4,197,944 | D. G. Catlin | Apr. 15, 1980 |
| 4,241,828 | P. A. Bourdelle et al. | Dec. 30, 1980 |
| 4,614,442 | G. W. Poncy | Sep. 30, 1986 |
| 4,684,018 | E. Järund | Aug. 4, 1987 |
| 4,757,381 | D. H. Cooper et al. | Jul. 12, 1988 |
| 4,823,949 | H. Bala | Apr. 25, 1989 |
| 5,069,337 | H. Bala | Dec. 3, 1991 |
| 5,667,068 | S. W. Weaver | Sep. 16, 1997 |
| 5,769,224 | R. Poncy et al. | Jun. 23, 1998 |
| 5,795,632 | M. Buchalter | Aug. 18, 1998 |
| 6,224,543 | C. E. Gammons et al. | May 1, 2001 |

Of these devices, that disclosed by Weaver ('068) is a protective cover for use in the storage of an endoscope. The protective cover is a tubular member defining a passageway running lengthwise through the member from end to end. A tapered portion is defined at one end for holding the endoscope in place as it is inserted into the passageway. A narrowed portion of the passageway is located at or near the distal end of the tubular member.

The '224 patent issued to R. Poncy et al., discloses a sterile packaging system for a pipetter sheath. The packaging system comprises two inner thermoplastic strips sandwiched between two outer paper covers. The inner strips and outer covers are connected along a tear seal formed by an electromagnetic heat sealer. The tear seal is generally in the shape of a pipetter such that the sheath is held in place by virtue of its conformity with the pipetter.

The remainder of the cited prior art disclose various embodiments of sheaths which are configured to cover the end of the probe. Specifically, the end of the sheath is closed.

By having a closed end, the medical probe is retained within the sheath without risk of the sheath being pulled over the probe. While many applications are conducive to the use of a probe whose distal end is enclosed within a sheath, there are many applications where the distal end of the medical instrument or probe must be unencumbered.

BRIEF SUMMARY OF THE INVENTION

The present invention is a cover for a medical probe or instrument. The medical probe cover is provided for being applied to the distal end of a medical probe or instrument such as an endoscope and is adapted to be received over the end of the medical probe in such a manner as to not require the application of a retainer, whereby the patient is subjected to minimal discomfort. Once received on the medical probe, the distal end of the medical probe and the exposed portion of the cover are disposed within a sterile field.

The cover generally defines an elongated tubular member having a first end and a second end. The cover defines a first panel member and a second panel member secured one to the other along their respective sides such that the first and second ends are open to define a tube. A throat is defined proximate the first end and is adapted to closely receive the distal end of the medical probe. The width of the throat is dimensioned to be less than half the circumference of the medical probe such that a tight fit is accomplished when the medical probe is inserted into the throat. The cover is fabricated from a material having elastomeric properties which allow it to stretch as the medical probe is inserted, and such that when stretched, the cover tends to return to its original shape thereby creating a tight bond between the cover and the medial probe to prevent removal of the cover.

The cover is tapered from the first end thereof to the throat to define a funnel configuration. Thus, as the medical probe is inserted into the cover, it is directed into and through the throat. The second end of the cover is then pulled to invert the cover up to the throat, thereby revealing the sterile inside surface of the cover and the distal end of the medical probe.

The first ends of each of the first and second panel members are defined with a double thickness of material, such as by folding over the respective panel member prior to heat sealing the panel members together as described above. The first panel member first end extends beyond the second panel member first end to define an extended portion. The extended portion of the first panel member provides a mechanism whereby the distal end of the medical probe is easily inserted into the first end of the cover. By placing the medical probe distal end on the extended portion, the first end of the cover is opened to allow insertion of the medical probe therein. The construction of the first ends, namely by folding to provide a double thickness, furthers the ease of opening the first end in the described manner. The second end of the cover is inverted to assist in the application of the cover of the medical probe.

To apply the cover of the present invention on a medical probe, the first end of the cover is engaged with the extension defined by the first panel member first end, thereby opening the first end of the cover. The medical probe is then inserted into the first end, through the throat and toward the second end of the cover. Once the throat is positioned on the medical probe at the desired location, the second end of the cover is inverted over the medical probe, thereby revealing the inside surface of the cover, which has heretofore remained untouched and sterile. The medical probe, having the cover of the present invention applied thereto, is then prepared for use.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
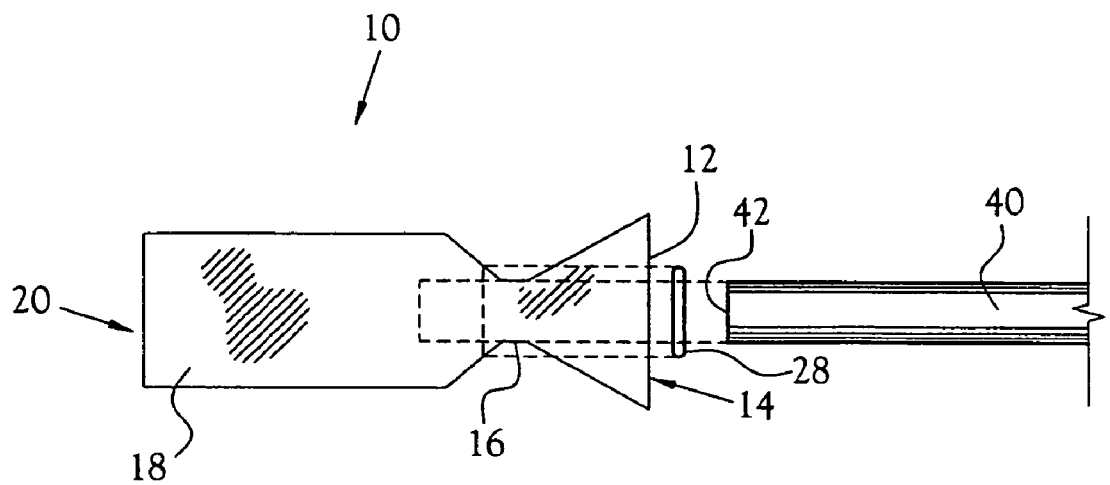
FIG. 1 is a top plan view of a prior art sheath.
Figure 2:
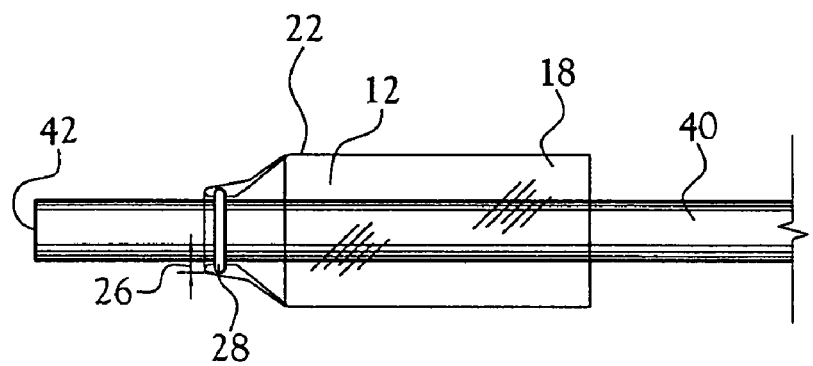
FIG. 2 is a top plan view of the prior art sheath of FIG. 1, shown being received on the end of a medical device, a retainer being received about the sheath to maintain the relative positions of the sheath and medical device.

A cover for a medical probe or instrument is disclosed. The medical probe cover of the present invention is illustrated generally at 110 in FIGS. 3-5. The medical probe cover, or cover 110, is provided for being applied to the distal end 42 of a medical probe 40 or instrument such as an endoscope. The cover 110 is adapted to be received over the end 42 of the medical probe 40 in such a manner as to not require the application of a retainer 28 (see PRIOR ART FIGS. 1 and 2), whereby the patient is subjected to minimal discomfort. Further, the cover 110 is configured such that once received on the medical probe 40, the distal end 42 thereof and the exposed portion of the cover 110 are disposed within a sterile field.

Figure 3:
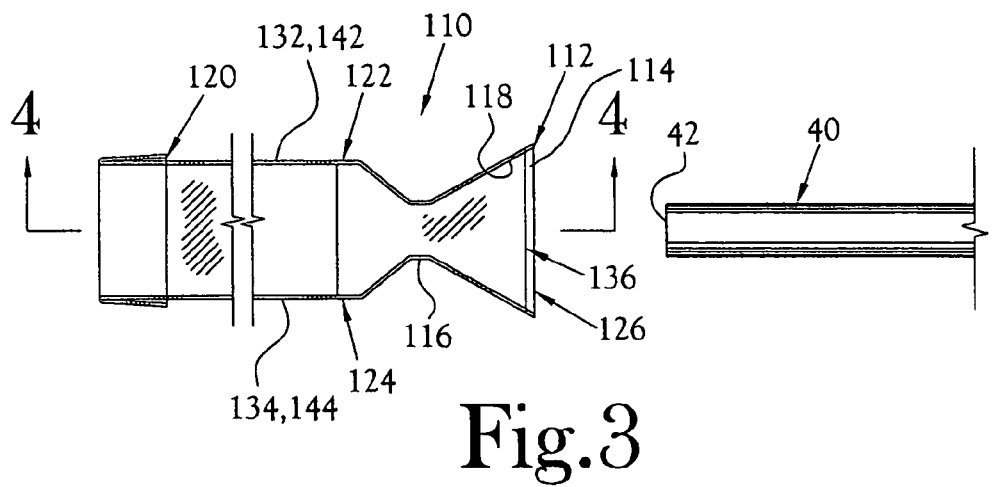
FIG. 3 is a top plan view of a reinforced probe cover of the present invention.
Figure 4:
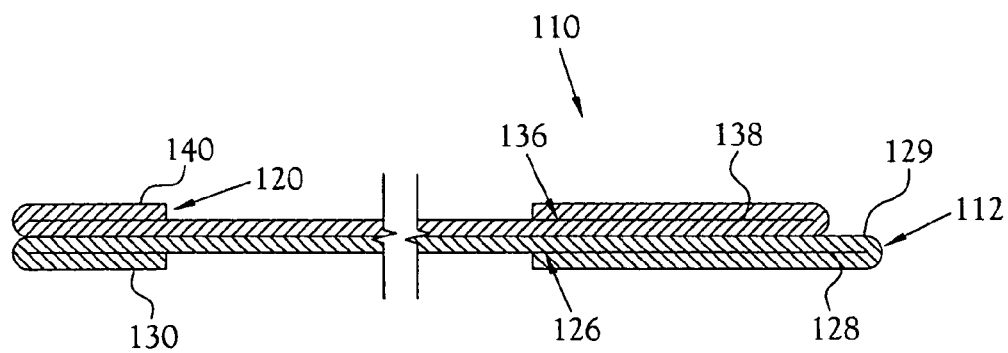
FIG. 4 is an elevation view of the reinforced probe cover of the present invention, in cross-section taken along 4-4 of FIG. 3.

FIG. 3 illustrates a top plan view of the cover 110 of the present invention. The cover 110 generally defines an elongated tubular member having a first end 112 and a second end 120, and a first side 122 and a second side 124. The cover 110 defines a first panel member 126 and a second panel member 136 secured one to the other along their respective first sides 132,142 and their respective second sides 134,144, whereby the first and second ends 112,120 are open to define a tube. As best illustrated in FIG. 4, the first and second panel members 126,136 each define first ends 128,138 and second ends 130,140, respectively, which are disposed proximate each other prior to securement of the first and second panel members 126,136. Referring again to FIG. 3, the first and second panel members 126,136 in the illustrated embodiment are secured one to the other using a conventional heat welding technique. However, it will be understood by those skilled in the art that other conventional techniques may be used.

A throat 116 is defined proximate the first end 112. The throat 116 is adapted to closely receive the distal end 42 of the medical probe 40. The width of the throat 116 is dimensioned to be less than half the circumference of the medical probe distal end 42 such that a tight fit is accomplished when the medical probe 40 is inserted into the throat 116. To this extent, the cover 110 is fabricated from a material having elastomeric properties which allow it to stretch as the medical probe 40 is inserted. Further, the elastomeric properties of the cover 110 create a memory, whereby when stretched, the cover 110 tends to return to its original shape. Thus, when the medical probe 40 is inserted into the throat 116 of the cover 110 and the throat 116 is stretched, it has a tendency to return to its original shape and size, thereby creating a tight bond between the cover 110 and the medial probe 40 to prevent unselected removal of the cover 110. In testing, a tensile strength of up to 0.96 lbs has been accomplished in the cover 110 of the present invention. As a result of the tensile strength accomplished in the present invention, as compared to the 0.35 lb tensile strength of the prior art covers 10 as discussed above, the need for a retainer has been obviated.

In the illustrated embodiment, the cover 110 is tapered from the first end 112 thereof to the throat 116 to define a funnel configuration 118, whereby as the medical probe 40 is inserted into the cover 110, it is directed into and through the throat 116. The second end 120 of the cover 110 is then pulled to invert the cover 110 up to the throat 116, thereby revealing the sterile inside surface of the cover 110 and the distal end 42 of the medical probe 40.

As best illustrated in FIG. 4, the first ends 128,138 of each of the first and second panel members 126,136 are defined with a double thickness of material. In the illustrated embodiment, each of the first and second panel member first ends 128,138 is defined by folding over the respective panel member 126,136 prior to heat sealing the panel members 126,136 together as described above.

In the illustrated embodiment, the first panel member first end 128 extends beyond the second panel member first end 138 to define an extended portion 129. The extended portion 129 of the first panel member 126 provides a mechanism whereby the distal end 42 of the medical probe 40 is easily inserted into an opening 114 defined by the first end 112 of the cover 110. By placing the medical probe distal end 42 on the extended portion 129, the first end opening 114 of the cover 110 is opened to allow insertion of the medical probe 40 therein. The construction of the first ends 128,138, namely by folding to provide a double thickness, furthers the ease of opening the first end opening 114 in the described manner.

In the illustrated embodiment, the second end 120 of the cover 110 is inverted to assist in the application of the cover 110 on the medical probe 40, as described below. However, it will be understood that the second end 120 may be disposed in various other configurations to assist in applying the cover 110 to a medical probe 40, to maintain the inner surface of the cover 110 as sterile until applied to the medical probe 40, and, especially for covers 110 adapted for longer probes 40, to reduce the overall length of the cover 110 prior to application on the probe 40.

Figure 5:
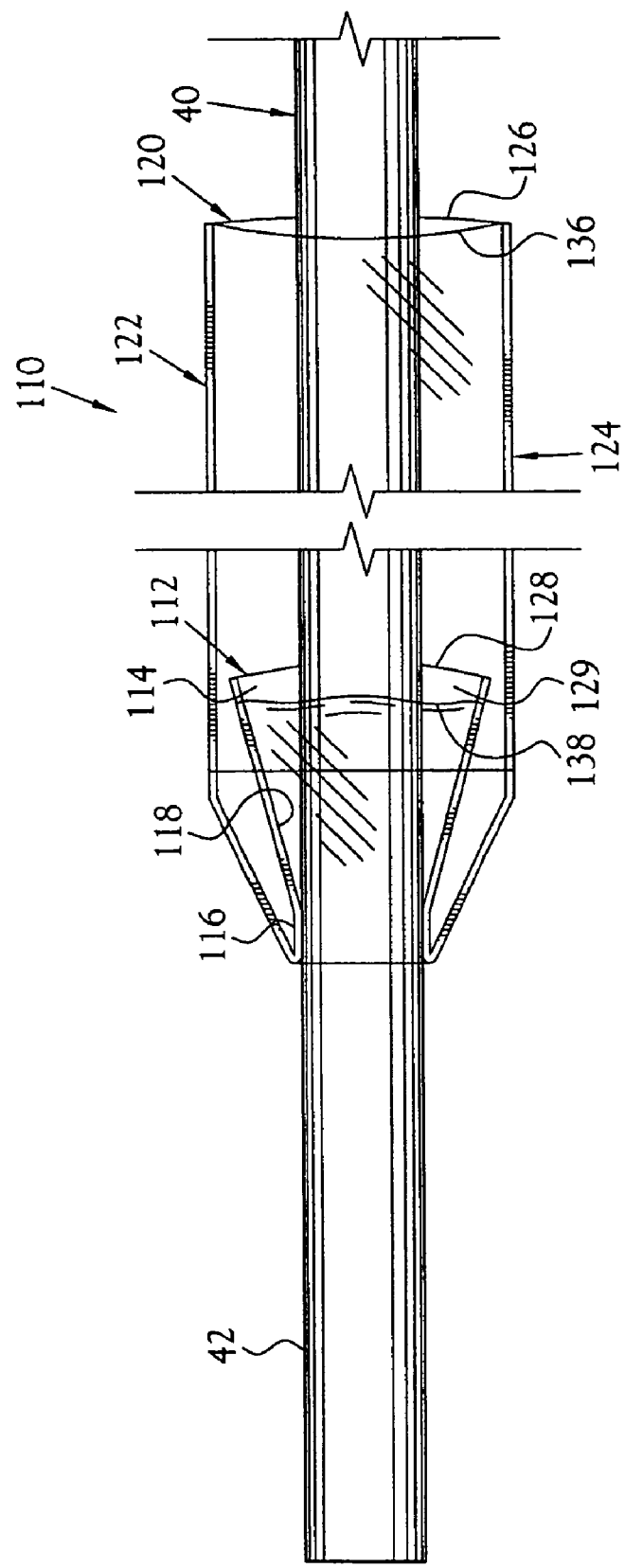
FIG. 5 is a top plan view of the reinforced probe cover of the present invention, shown being received on a medical probe.

FIG. 5 best illustrates the application of the cover 110 of the present invention. The first end 112 of the cover 110 is engaged with the extended portion 129 defined by the first panel member first end 128, thereby opening the first end opening 114 of the cover 110. The medical probe 40 is then inserted into the first end opening 114, through the throat 116 and toward the second end 120 of the cover 110. Once the throat 116 is positioned on the medical probe 40 at the desired location, the second end 120 of the cover 110 is inverted over the medical probe 40, thereby revealing the inside surface of the cover 110, which has heretofore remained untouched and sterile. The medical probe 40, having the cover 110 of the present invention applied thereto, is then prepared for use.

From the foregoing description, it will be recognized by those skilled in the art that a medical probe cover adapted to be received on a medical probe has been provided. The medical probe cover is provided for being applied to the distal end of a medical probe or instrument such as an endoscope in such a manner as to not require the application of a retainer, whereby the patient is subjected to minimal discomfort. The cover is configured such that once received on the medical probe, the distal end of the medical probe and the exposed portion of the cover are disposed within a sterile field While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

I claim:

1. A cover for a medical probe comprising:
a first panel member defining a first side, a second side, a first end and a second end; and
a second panel member defining a first side, a second side, a first end and a second end, said first panel first side and said second panel first side being secured one to another and said first panel second side and said second panel second side being secured one to another whereby said cover defines a tubular configuration having a cover first end and a cover second end, said first panel first end being folded over prior to securement to said second panel member to define a double thickness, and said second panel member first end being folded over prior to securement to said first panel member to define a double thickness; and
a throat defined proximate said cover first end and within a region where said first panel member defines said double thickness and said second panel member defines said double thickness, said cover being tapered from said cover first end to said throat to define a funnel configuration, said throat being adapted to closely receive a distal end of a medical probe said double thickness of each of said first and second panel members providing sufficient resiliency to maintain said cover on the distal end of a medical probe without necessitating further retaining means, whereby as a medical probe is inserted into said cover and directed into and through said throat, and as said cover second end is pulled to invert said cover up to said throat, a sterile inside surface of said cover and a distal end of the medical probe are revealed.

2. The cover of claim 1 wherein said throat defines a width adapted to be less than one-half the circumference of the medical probe distal end.

3. The cover of claim 1 wherein said cover first end defines a funnel configuration from said cover first end to said throat, whereby the medical probe distal end is directed toward said throat upon insertion into said cover first end.

4. The cover of claim 1 wherein said first panel member first end extends beyond said second panel member first end, an extended portion being defined between said first panel member first end and said second panel member first end to facilitate opening said cover first end.

5. The cover of claim 1 wherein said cover second end is at least partially inverted to facilitate application of said cover on the medical probe.

6. The cover of claim 1 wherein said cover is fabricated from a material having elastomeric properties whereby said cover returns to an initial size and shape after being stretched.

7. A cover for a medical probe comprising:
   a first panel member defining a first side, a second side, a first end and a second end;
   a second panel member defining a first side, a second side, a first end and a second end, said first panel first side and said second panel first side being secured one to another and said first panel second side and said second panel second side being secured one to another whereby said cover defines a tubular configuration having a cover first end and a cover second end, said first panel first end being folded over prior to securement to said second panel member to define a double thickness, and said second panel member first end being folded over prior to securement to said first panel member to define a double thickness, said first panel member first end extending beyond said second panel member first end, an extended portion being defined between said first panel member first end and said second panel member first end to facilitate opening said cover first end; and
   a throat defined proximate said cover first end and within a region where said first panel member defines said double thickness and said second panel member defines said double thickness, said cover being tapered from said cover first end to said throat to define a funnel configuration, said throat being adapted to closely receive a distal end of a medical probe said double thickness of each of said first and second panel members providing sufficient resiliency to maintain said cover on the distal end of a medical probe without necessitating further retaining means, whereby as a medical probe is inserted into said cover and directed into and through said throat, and as said cover second end is pulled to invert said cover up to said throat, a sterile inside surface of said cover and a distal end of the medical probe are revealed.

8. The cover of claim 7 wherein said throat defines a width adapted to be less than one-half the circumference of the medical probe distal end.

9. The cover of claim 7 wherein said cover first end defines a funnel configuration from said cover first end to said throat, whereby the medical probe distal end is directed toward said throat upon insertion into said cover first end.

10. The cover of claim 7 wherein said cover second end is at least partially inverted to facilitate application of said cover on the medical probe.

11. The cover of claim 7 wherein said cover is fabricated from a material having elastomeric properties whereby said cover returns to an initial size and shape after being stretched.

12. A method for fabricating a cover for a medical probe, said method comprising the steps of:
   (a) providing a first panel member defining a first end and a second end;
   (b) folding said first panel member first end under said first panel member to define a double thickness;
   (c) positioning a second panel member defining a first end and a second end over said first panel member;
   (d) folding said second panel member first end over said second panel member to define a double thickness; and
   (e) securing said first panel member and said second panel member to define a cover first side and a cover second side, whereby a tubular configuration having a cover first end and a cover second end is defined, said step of securing said first panel member and said second panel member including the step of defining a throat proximate said cover first end and within a region in which said first panel member defines said double thickness and said second panel member defines said double thickness, said cover being tapered from said cover first end to said throat to define a funnel configuration said throat being adapted to closely receive a distal end of a medical probe said double thickness of each of said first and second panel members providing sufficient resiliency to maintain said cover on the distal end of the medical probe without necessitating further retaining means, whereby as a medical probe is inserted into said cover and directed into and through said throat, and as said cover second end is pulled to invert said cover up to said throat, a sterile inside surface of said cover and a distal end of the medical probe are revealed.

13. The method of claim 12 wherein said throat defines a width adapted to be less than one-half the circumference of the medical probe distal end.

14. The method of claim 12 wherein said step of securing said first panel member and said second panel member further includes the step of defining a funnel configuration from said cover first end to said throat, whereby the medical probe distal end is directed toward said throat upon insertion into said cover first end.

15. The method of claim 12 wherein said step of folding said second panel member first end includes the step of defining an extended portion of said first panel member first end by folding said second panel member first end such that said first panel member first end extends beyond said second panel member first end.

16. The method of claim 12 further including the step of inverting at least a portion of said cover second end to facilitate application of said cover on the medical probe.

* * * * *

UNITED STATES PATENT AND TRADEMARK OFFICE
Certificate

Patent No. 7,357,788 B2                                                                           Patented: April 15, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Clifford Eugene Gammons, Loudon, TN (US); and Lawrence S. Polayes, Morgan Hill, CA.

Signed and Sealed this Twelfth Day of March 2013.

NICHOLAS D. LUCCHESI
*Supervisory Patent Examiner*
Art Unit 3763
Technology Center 3700